(12) United States Patent
Lubahn et al.

(10) Patent No.: US 7,550,466 B2
(45) Date of Patent: Jun. 23, 2009

(54) ALPHA AND/OR β-ADRENERGIC ANTAGONISTS AND AGONISTS TO TREAT PAIN

(75) Inventors: Cheri Lubahn, Glendale, AZ (US); Dianne Lorton, Avondale, AZ (US)

(73) Assignee: Sun Health Research Institute, Sun City, AZ (US)

( * ) Notice: Subject to any disclaimer, the term of this patent is extended or adjusted under 35 U.S.C. 154(b) by 0 days.

(21) Appl. No.: 11/872,622

(22) Filed: Oct. 15, 2007

(65) Prior Publication Data

US 2008/0153830 A1    Jun. 26, 2008

Related U.S. Application Data

(63) Continuation-in-part of application No. 10/928,437, filed on Aug. 27, 2004, now Pat. No. 7,462,618.

(60) Provisional application No. 60/851,680, filed on Oct. 13, 2006, provisional application No. 60/498,367, filed on Aug. 27, 2003.

(51) Int. Cl.
| A61K 31/50 | (2006.01) |
| A61K 31/52 | (2006.01) |
| A61K 31/415 | (2006.01) |
| A61K 31/335 | (2006.01) |
| A61K 31/135 | (2006.01) |

(52) U.S. Cl. .............. 514/252.01; 514/263.1; 514/392; 514/400; 514/449; 514/649; 514/653

(58) Field of Classification Search ........... 514/252, 514/263, 392, 400, 449, 649, 653
See application file for complete search history.

(56) References Cited

U.S. PATENT DOCUMENTS 5,070,084 A * 12/1991 Campbell ............ 514/248
5,541,188 A * 7/1996 Maltin ............ 514/263.34

* cited by examiner

*Primary Examiner*—Raymond J Henley, III
(74) *Attorney, Agent, or Firm*—Jennings, Strouss & Salmon; Joseph W. Mott (57) ABSTRACT

The present disclosure provides for improved methods for treating pain, including pain associated with chronic inflammatory diseases, neuropathic pain and cancer by using α-adrenergic antagonists and β-adrenergic agonists (particularly $β_2$-adrenergic agonists) alone or in combination.

25 Claims, 6 Drawing Sheets

# ALPHA AND/OR β-ADRENERGIC ANTAGONISTS AND AGONISTS TO TREAT PAIN

CLAIM TO DOMESTIC PRIORITY

This application claims the benefit of priority of U.S. Application Ser. No. 60/851,680 filed on Oct. 13, 2006, and is a continuation-in-part of U.S. application Ser. No. 10/928,437, filed on Aug. 27, 2004, now issued U.S. Pat. No. 7,462,618, which claims the benefit of priority of U.S. Application Ser. No. 60/498,367, filed Aug. 27, 2003.

FIELD OF THE INVENTION

The present invention relates to improved methods for the treatment of pain that occurs in, but is not limited to, rheumatoid arthritis, other inflammatory autoimmune diseases, neuropathic pain, and cancer. The invention relates to the use of α-adrenergic antagonists and β-adrenergic agonists (particularly $\beta_2$-adrenergic agonists), alone or in combination, in treating pain.

BACKGROUND OF THE INVENTION

The most common symptom for which patients seek medical help is pain. Pain can be classified as either acute or chronic. Acute pain results from immediate tissue injury and is self-limited. Acute pain is a natural defense mechanism in response to immediate tissue injury and functions to induce withdrawal from the painful stimulus and to prevent further use of the injured body part to allow the damaged tissue to heal. Acute pain is amenable to traditional pain medications and therapeutics. These include non-steroidal anti-inflammatory drugs (NSAIDs) and opioids. In contrast to acute pain, chronic pain is present for an extended period of time (e.g., three or more months) that persists in the absence of the tissue damage that initiated the pain response. Chronic pain can lead to significant changes in a patient's quality of life and functional ability.

Chronic pain is a significant medical problem for which the efficacy of current treatments is dismal. In the United States it is estimated that 40 million people suffer from chronic recurrent headaches; 35 million people are afflicted with persistent back pain; 20 and 2.1 million people have severe pain associated with osteoarthritis and rheumatoid arthritis, respectively; and 5 million people suffer from cancer-related pain.

DETAILED DESCRIPTION OF VARIOUS EMBODIMENTS

This present disclosure provides for a novel method for the treatment of patients diagnosed with pain. Pain can be classified as being "nociceptive pain" or "neuropathic pain." Nociceptive pain occurs as a result of activation of pain-sensitive nerve fibers, either somatic or visceral. This type of pain is usually in response to direct tissue damage. Nociceptive pain results from the release of several substances, including bradykinin, serotonin, substance P, histamine, and prostaglandins in the area of tissue damage that activates the pain-sensitive nerve fibers. In the case of nociceptive pain occurring from activated somatic nerves, the pain is typically experienced as an aching or pressure-like sensation. In contrast, neuropathic pain refers to pain that is due to injury or disease of the central or peripheral nervous system. Unlike the immediate pain caused by tissue injury, neuropathic pain often becomes long lasting or chronic. Neuropathic pain also can occur spontaneously. Neuropathic pain is often accompanied by perception of pain from normally innocuous stimuli (allodynia) and increased pain from normally mildly noxious stimuli (hyperalgesia). In humans with neuropathic pain, prevalent symptoms include cold hyperalgesia and mechanical allodynia. Pain associated with neuropathic pain frequently described as being "lancinating," "burning," or "electric". In North America, approximately 4 million people suffer from chronic neuropathic pain. Adequate pain control is achieved in less than half of these patients.

Neuopathic pain syndromes can result from disease progression (e.g., diabetic neuropathy, multiple sclerosis, post-herpetic neuralgia, or rheumatoid arthritis), injury (e.g., amputation (phantom-limb pain), or injuries sustained in an accident (avulsions), and nerve damage (e.g., chronic alcoholism, viral infection, hypothyroidism, uremia, vitamin deficiencies). Other causes of neuropathic pain include traumatic nerve injuries that cause neuromas, in which aberrant nerve regeneration results in pain. Neuropathic pain can also result from injury associated with stroke and from spinal cord injury.

In cancer patients, tumor growth compression of adjacent nerves, brain, spinal cord and/or cancer therapy (chemotherapy and radiation therapy) induced damage can cause nerve damage that results in development of neuropathic pain. In general, long-lasting somatic pain results form inflammatory responses that occur in response to tissue injury, including nerve entrapment, surgical procedures, cancer and arthritis (2). Inflammatory pain is currently treated with NSAIDs; however, there is great room for improvement for these treatments.

A complex series of biochemical and cellular events that are activated in response to tissue injury or in the presence of foreign substances induces inflammatory processes. Inflammatory responses occur at sites of tissue injury or where foreign materials are present. Inflammatory responses, in general, contribute to tissue repair and healing and assist with removal of foreign material. Erythema (redness), heat, edema (swelling), pain and loss of function are cardinal signs of inflammation. In general, inflammatory pain does not induce a continuous painful response. Pain generally occurs when the inflamed site is moved or touched.

Tissue injury results in the release of inflammatory mediators, such as bradykinin, histamine, serotonin (5-HT), ATP and nitric oxide, from damaged cells. The arachidonic acid (AA) pathway becomes activated and results in the production of prostaglandins and leukotrienes. AA is converted to prostaglandins through activation of phospholipase A2 and cyclooxygenases (COX-1 and COX-2). The NSAIDS exert their analgesic properties by inhibiting COX-1 and/or COX-2, thus blocking conversion of AA to prostaglandins.

These early events result in the recruitment of immune cells to the site of tissue injury by inducing changes in vascular permeability and expression of chemotactic factors and adhesion molecules by the vascular endothelium and cells involved in innate immunity (e.g., neutrophils and monocytes). Recruited immune cells produce and release further inflammatory mediators, including cytokines and growth factors. Some of the inflammatory mediators that are produced activate nociceptors directly (e.g., bradykinin) and thus, lead to spontaneous pain. Other inflammatory mediators indirectly induce pain via inflammatory cells, stimulating release of additional pain inducing (algogenic) substances. Pain, inflammation and hyperalgesia (increased responsiveness to normally noxious stimuli) are induced upon application of inflammatory mediators (e.g., bradykinin, growth factors, prostaglandins).

In the periphery, pro-inflammatory cytokines produced by immune cells exert direct excitatory effects on sensory afferents. Cytokines also are transported centrally where they further sensitize pain transmission. In the spinal cord, microglia become activated after peripheral nerve injury and produce inflammatory mediators, including the cytokines, TNF and IL-1. Activated microglia induce central sensitization and may underlie extension of pain to the contralateral side, so-called mirror image pain.

The type of pain treated by the presently disclosed composition and method can be any type of pain, and preferably pain selected from neuropathic pain, nociceptive pain, chronic pain, pain associated with cancer, chronic pain associated with fibromyalgia, and pain associated with chronic inflammation, including but not limited to rheumatic diseases. This novel treatment comprises treatment with a combined use of a β-adrenergic agonist (preferably a $β_2$-adrenergic agonist) and an α-adrenergic antagonist (preferably a non-selective α-adrenergic).

This method comprises the administration of an effective dose of a β-adrenergic agonist (preferably a $β_2$-adrenergic agonist) and an α-adrenergic antagonist (preferably a non-selective α-adrenergic antagonist) to patients with pain. Even more particularly, the method of the present invention comprises the administration of an effective dose of the $β_2$-adrenergic agonist terbutaline coupled with an effective dose of the α-adrenergic antagonist, phentolamine (or more specifically nonselective α-adrenergic antagonists) to patients with pain.

Specifically, the present disclosure provides novel methods for treating pain by targeting the SNS. The present disclosure addresses one or more short-comings or disadvantages in the available treatment regimens for neuropathic pain through the use of a combination of β-adrenergic agonists and α-adrenergic antagonists. In alternate embodiments, the disclosure contemplates the use of $β_2$-adrenergic agonists and non-specific α-, $α_2$- or $α_1$-adrenergic antagonists, and particularly terbutaline, phentolamine and prazosin, respectively, as agents to treat patients with neuropathic pain.

The disclosure provides for β-adrenergic agonists in combination with α-adrenergic antagonists will be particularly useful in treating neuropathic pain, as this combination of drugs effectively up-regulates inhibitory pathways that effectively dampen pain responses, the descending inhibitory noradrenergic innervation to the dorsal spinal cord. In certain embodiments, the present disclosure concerns a method for treating neuropathic pain by the application of a therapeutically effective dose of a β-adrenergic agonist, and preferably a $β_2$-adrenergic agonist such as terbutaline, coupled with a therapeutically effective dose of an α-,$α_2$- or $α_1$-adrenergic antagonist, and preferably phentolamine or prazosin, to human subjects with the disease.

As used herein, the term "treating neuropathic pain by the application of a therapeutically effective dose of a β-adrenergic agonist" and "a therapeutically effective dose of an α- or $α_1$-adrenergic antagonist" are used to signify that the β-adrenergic agonist and α-adrenergic antagonist are supplied to the patient in amounts, and for a period of time, that are effective to provide improvement in one or more of the clinically measured parameters of neuropathic pain, particularly disease parameters of hyperalgesia and/or allodynia.

In the present methods for treating pain, the type of pain can be any type of pain, and preferably pain selected from neuropathic pain, nociceptive pain, chronic pain, pain associated with cancer, chronic pain associated with fibromyalgia, and pain associated with chronic inflammation, including but not limited to rheumatic diseases.

To determine whether there has been an improvement in one or more of the clinically measured parameters of the neuropathic pain, one would determine the value of such a parameter in a given patient both before and during treatment. Various clinical signs and symptoms are known by those known to be skilled in the art as suitable markers of neuropathic pain.

The adrenergic agents of the present disclosure are safer and have fewer side effects than drugs currently being used to treat neuropathic pain. Accordingly, $β_2$-adrenergic agonists considered to be of use in the present disclosure include metaproterenol, albuterol, isoetharine, pirbuterol, bitoltrol, ritodrine, or salbutamol, and preferably, terbutaline. The α-adrenergic antagonists considered to be of use in this disclosure include phentolamine, regitine, prazosin, doxazosin, tamsulosin, or terazosin. The β-agonists and α-antagonists may be administered to the patient in any pharmaceutically acceptable vehicle and by any route heretofore acceptable for these agents. The preferred route of administration is orally, although one may, if desired, choose to administer the agonists or antagonists intravenously, sublingually, intramuscularly, subcutaneously, or in a sustained release form.

As will be understood by those skilled in the art, the effective doses of the β-agonist and α-antagonist will depend upon the route of administration and the patient's sensitivity to the particular β- (or $β_2$-) and α- (or $α_1$-) adrenergic antagonist and agonist, respectively. Recommended doses for both the β and α-adrenergic agonist and antagonist, respectively, range from about 1.0 to 10.0 mg, with a preferred range of about 2.0 to 5.0 mg, or even more preferably about 1.25 to 2.5 mg given three times per day depending upon disease severity and patient responses to the drugs. The dosages may be more effectively adjusted on an individual basis as pain severity varies from patient to patient.

As disclosed herein, a combination of both these drugs is effective in increasing descending noradrenergic inhibitory pathways that inhibit pain processing in the spinal cord. Such effect is known to ameliorate pain and could be potentially used to treat pain disorders, particularly rheumatoid arthritis. Other $\beta_2$-adrenergic agonists useful in this novel method of treatment include: metaproterenol, albuterol, isoetharine, pributerol, bitolterol, ritodrine, and salmeterol. Other $\alpha$-adrenergic agonists useful in this novel method of treatment include: regitine, prazosin, doxazosin, tamsulosin, and terazosin.

The $\beta$- (or $\beta_2$-) and $\alpha$- (non-selective $\alpha$-, $\alpha_2$- or $\alpha_1$-) adrenergic agonist and antagonist, respectively, exert a suppressive effect on pain. The SNS can act to exacerbate some neuropathic pain states through the release of norepinephrine (NE) and its action via a number of mechanisms. These include but are not limited to action through a novel expression of excitatory $\alpha$-adrenoceptors on nociceptors, actions via sprouting of sympathetic fibers to surround sensory afferent terminals and cell bodies and effects on immune cells. Additionally, manipulation of the SNS using adrenergic $\beta_2$-agonists and $\alpha$-antagonists in combination induces an up-regulation of the inhibitory central descending noradrenergic innervation to dorsal horn spinal cord, where pain information is processed.

With peripheral nerve injury both sensory and sympathetic nerves are damaged. Some of the sympathetic nerves die back as a result of injury, essentially causing a partial denervation of the target tissues. With this sympathetic nerve loss, this reduces the availability of NE for interaction with $\beta_2$- and $\alpha$-adrenoceptors expressed on target immune and vascular cells at the site of injury. The $\beta$-agonists replace the function of the lost sympathetic nerve fibers that occurs with nerve injury. Stimulation of $\beta_2$-adrenoceptor causes a hyperpolarization of DRG neurons and reduces their excitability to other stimuli, and thus would be expected to provide some of the analgesic properties of the proposed combined adrenergic treatment. Additionally, stimulating macrophage and lymphocyte $\beta_2$-adreneoceptors has the added benefit of inhibiting production of specific inflammatory cytokines by macrophages (e.g., TNF$\alpha$ and IL-1) and/or T helper lymphocytes that promote inflammation and promote production of anti-inflammatory cytokines by these same immune cells (e.g., IL-10, IL-13 and IL-4). Proinflammatory cytokines at the injury site are also responsible for pain amplification after peripheral nerve injury.

Finally, $\beta$-agonists induce production of nerve growth factor that is required for re-growth of injured primary afferent and sympathetic neurons. Thus, treatment with the $\beta_2$-agonists is postulated to restore innervation of injured sympathetic and sensory nerves in the periphery and reduce mediators that promote pain. NGF produced in response to the nerve injury is retrogradely transported from the periphery to the cell bodies of the DRG neurons and is released into the spinal cord by primary sensory axons. This provides nerve growth factor that promotes the increase in noradrenergic innervation of the dorsal spinal cord. An increase in $\beta_2$-agonist-induced NGF production at the injury site results in greater NGF transport via primary sensory afferent nerves into the dorsal horn providing additional trophic support for growth of descending noradrenergic axons into the dorsal horn. This increased noradrenergic innervation exerts a greater analgesic effect.

As for the $\beta_2$-agonist, the function of the $\alpha$-adrenergic antagonist in the combined treatment is by several mechanisms. The $\alpha$-antagonist blocks the catecholamine stimulation of the $\alpha_2$ and $\alpha_1$-adrenoceptors expressed on primary sensory neurons depolarize these neurons to induce pain responses. Additionally, the $\alpha$-antagonist blocks stimulation of activated macrophage $\alpha$-adrenergic receptors by catecholamines, either norepinephrine or epinephrine, which promote production of proinflammatory mediators that are critically involved in induction and maintenance of pathological pain.

Finally, the $\alpha$-antagonists further increase the production of NGF at the nerve injury site, as stimulation of $\alpha$-adrenoceptors inhibit NGF production. This promotes retrograde transport of higher concentrations of NGF by primary sensory afferent nerves into the spinal cord, and thus increases the growth of descending noradrenergic nerves into the dorsal spinal cord. In this manner, $\beta_2$-adrenergic agonists coupled with $\alpha$-adrenergic antagonists are analgesics when combined for treating pathological pain.

The following example is included to demonstrate preferred embodiments of the invention. It should be appreciated by those of skill in the art that the techniques disclosed in the example which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Combined $\beta_2$-Adrenergic Agonist (Terbutaline) and $\alpha$-Adrenergic Antagonist Suppression of Pain in the Adjuvant-Induced Arthritis Pain Model in Rats Methods. Lewis rats with adjuvant-induced arthritis (AA), a model of rheumatoid arthritis and chronic pain, were used to examine the combined action of the $\beta_2$-adrenergic agonist terbutaline and the $\alpha$-adrenergic antagonist phentolamine for treating chronic pain. AA is known to be induced in rats by an intradermal injection of Complete Freund's Adjuvant (CFA; 0.3 mg M. Butyricum/0.1 ml, suspended in sterile mineral oil) at the base of the tail. In this case, adult male Lewis rats (250-300 gm) were immunized intradermally with CFA to induce arthritis. Signs of arthritis were observed between eight to ten days following adjuvant injections.

Terbutaline, (1.2 mg/Kg/day) an $\beta_2$-agonist, and phentolamine (5 mg/Kg/day), an $\alpha$-adrenergic receptor antagonist, were administered starting 12 days post-CFA injection (just after onset of AA) and continued daily until sacrifice at day 28 post-CFA. The terbutaline and phentolamine were freshly prepared prior to each injection in 0.01 M ascorbic acid and administered by i.p. injection twice a day. Control rats were injected with vehicle using the same schedule. Non-arthritic untreated rats were used to determine normal base line values for parameters being measured.

Animals were examined for disease severity using dorsoplantar swelling over the course of 28 days and X-ray analysis on day 28. Rats were monitored for disease progression every other day after CFA challenge until day 10, and then daily until the end of the experiment. Dorsoplantar swelling was assessed using a Mitutoyo Corp. dial thickness gauge to measure hind paw thickness. Differences in dorsoplantar swelling between treatment groups were determined by ANOVA with repeated measures and Neuman-Keuls post hoc analysis. X-rays were evaluated using a grading scale described in Ackerman N R, Rooks W H 2nd, Shott L, Genant H, Maloney P, West E. 1979. Effects of naproxen on connective tissue changes in the adjuvant arthritic rat. *Arthritis Rheum* 22:1365-74, without knowledge of the treatment group. The radiograms were evaluated for (1) swelling; (2) osteoporosis; (3) cartilage loss; (4) erosions; and (5) heterotopic ossification-proliferation of new bone. A subjective 0-4 grading scale was used with 0 indicating negative or normal joint conditions, 1 indicating minimal pathology, 2 mildly arthritic joint, 3 moderately arthritic joint, and 4 severely arthritic joint. Radiographic scores were averaged among animals in the same treatment groups, and subjected to a Friedman test or Kruskal-Wallis statistical analysis.

On day 28 of the study, rats were anesthetized with Chlorohydrate (8% solution 1.0 ml/100 gm body wt) and perfused transcardially with phosphate-buffered saline (pH 7.2) followed by 250 ml of 4% paraformaldehyde with picric acid in the same buffer. The cervical spinal cord was dissected from rats in each of the treatment groups, post-fixed in the perfusion fixative for 24 h at $4°$ C., and transferred at 24 h increments into 10, 20 and 30% sucrose (pH 7.4)/PBS buffer at $4°$ C. Spleens were frozen on dry ice and then stored at $-80°$ C. until sectioning.

Tissue preparation. Frozen tissue blocks were mounted onto the freezing chuck of a sliding microtome, and 30 µm sections were cut and placed into 0.15 M phosphate buffer (pH 7.4). Spinal cord sections then were transferred into a cryoprotectant solution at $4°$ C. for 24 hours and/or stored at $-20°$ C. until immunocytochemical (ICC) staining.

ICC staining. ICC for tyrosine hydroxylase (TH), the rate limiting enzyme for the synthesis of NE, and dopamine-β-hydroxylase (DBH) was performed using an anti-TH antibody (1:1000; Chemicon) or anti-DBH antibody (1:500 Chemicon) with nickel intensification of the 3,3'-diaminobenzidine (0.04%; DAB) chromagen reaction product to form a blue/black reaction product. All steps were carried out in 0.15 M phosphate buffer (pH 7.4) at $25°$ C. using gentle agitation, unless otherwise indicated. Sections were rinsed thoroughly in buffer and incubated for 30 minutes in 4% normal goat serum (NS). The primary antibody was diluted in 0.4% Triton X-100 in 0.15 M phosphate buffer containing 0.25% bovine serum albumin. Incubation in the primary antibody was carried out at $4°$ C. for 48 hours. Control sections were incubated in primary antibody buffer in the absence of the primary antibody.

On day 2, sections were rinsed 6×7 minutes in buffer, and incubated for 30 minutes in 10% NS, and then incubated in the secondary goat-anti rabbit antibody (Vector) diluted in buffer (1:2000) for 90 minutes. Sections then were rinsed 2×7 minutes in buffer and incubated in 2.5% methanol with 8% hydrogen peroxide for 20 minutes to remove endogenous peroxidase activity. Following six 7 minutes rinses, sections were incubated in an avidin-biotin-peroxidase complex (ABC) (Vector Elite kit: 1:4000 dilution in buffer) for 90 minutes. Sections were rinsed 4×7 minutes in buffer, followed by 2×7 minutes in 0.05 M acetate-imidazole, pH 7.4, and then developed in acetate-imidazole buffer containing 0.25 g/100 ml nickel (II) sulfate, 0.04 gm/100 ml DAB, and 0.005% hydrogen peroxide for 10 minutes. All sections then were rinsed 2×7 minutes in acetate-imidazole buffer, followed by 4×7 minutes rinses in buffer, mounted on gelatin-coated slides, dried, dehydrated through a series of graded ethanols, cleared in xylene, and cover-slipped in Permount. Stained sections were examined and photographed on a Zeiss Axioskop microscope. Digital images were captured using a Nikon-D50 camera attached to the microscope. Images were saved at 600 dpi, adjusted for contrast and brightness.

Quantification of TH- and DBH-immunoreactivity. A total of 4 and 6 rats from each treatment group were used for quantification of TH- and DBH-immunoreactivity, respectively. Cervical spinal cord sections were randomly selected. Images of the dorsal horn axon staining for each antibody were captured at ×200 magnification using a Nikon D-50 camera and captured to a computer via a USB port using the Nikon Capture software program. Effect of the combined treatment on the extent of descending noradrenergic innervation to the cervical spinal cord dorsal horn was assessed using ImagePro Plus software to determine the numbers of TH- and DBH-positive axons present in the dorsal horn. The number of digitized pixels positive for TH or DBH in a fixed area from three sections taken within LI-LIII were taken.

The more intense and abundant the TH- or DBH-immunoreactivity the greater were the number of digitized pixels covering these profile images, thus obtaining a greater value of pixel number per area. The ratio of TH/DBH positive pixels per total possible pixels were determined for each of the three samples for each spinal cord section were determined and averaged to obtain a section mean. Section means from three sections per rat were averaged to obtain a mean ratio of TH/DBH positive area/total area in the dorsal spinal cord overlying TH- or DBH-immunoreactive axons for each animal in the study. Means for animals in each treatment group were averaged to obtain group means for comparison. Values were expressed as group means±the S.E.M. Amount of specific TH and DBH staining was compared between treatment groups using a one-way ANOVA with Bonferroni multivariate analysis. Significance level was set at $P<0.05$.

Figure 1:
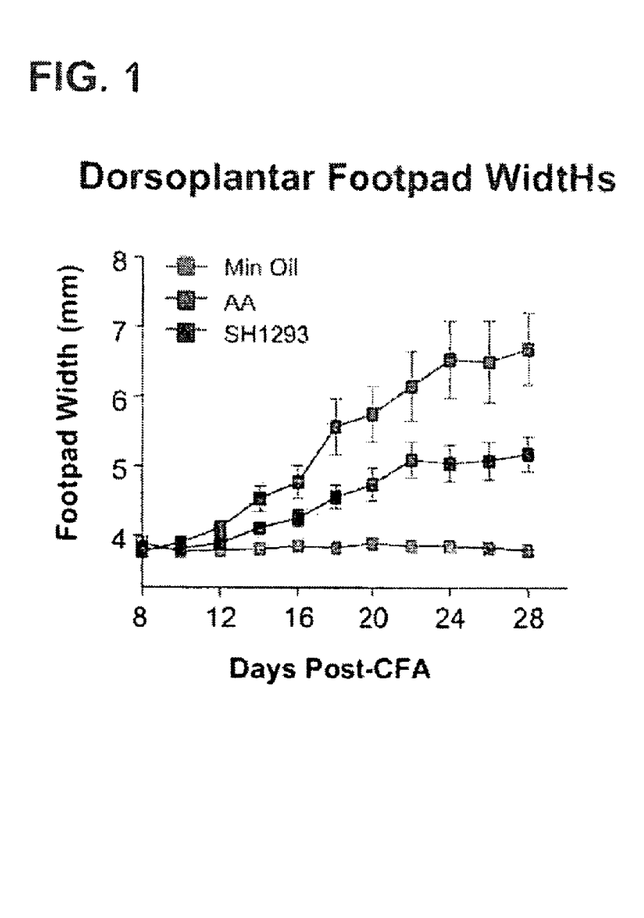
FIG. 1 is a graph demonstrating the anti-inflammatory effects of combined terbutaline and phentolamine treatment on dorsoplantar swelling in arachidonic acid (AA) rats compared to vehicle-treated AA rats.

Results. As shown in FIG. 1, combination treatment had a greater effect in reducing dorsoplantar swelling than either drug alone significantly reducing dorsoplantar swelling by day 28. FIG. 1 is a graph demonstrating the anti-inflammatory effects of combined terbutaline and phentolamine treatment on dorsoplantar swelling in AA rats compared to vehicle-treated AA rats. Untreated non-arthritic rats were used to obtain baseline data. Mean hind limb dorsoplantar widths from arthritic rats treated with twice daily injections of: (1) vehicle or (2) terbutaline and phentolamine to AA rats and of (3) non-arthritic untreated rats. Footpad widths of hind limbs of AA rats treated with saline compared to terbutaline and phentolamine are significantly different from day 22 to day 28. Footpad widths for both AA groups are significantly different from the non-arthritic mineral oil-treated rats from day 13 Post-CFA through day 28 ($P<0.001$).

Figure 2:
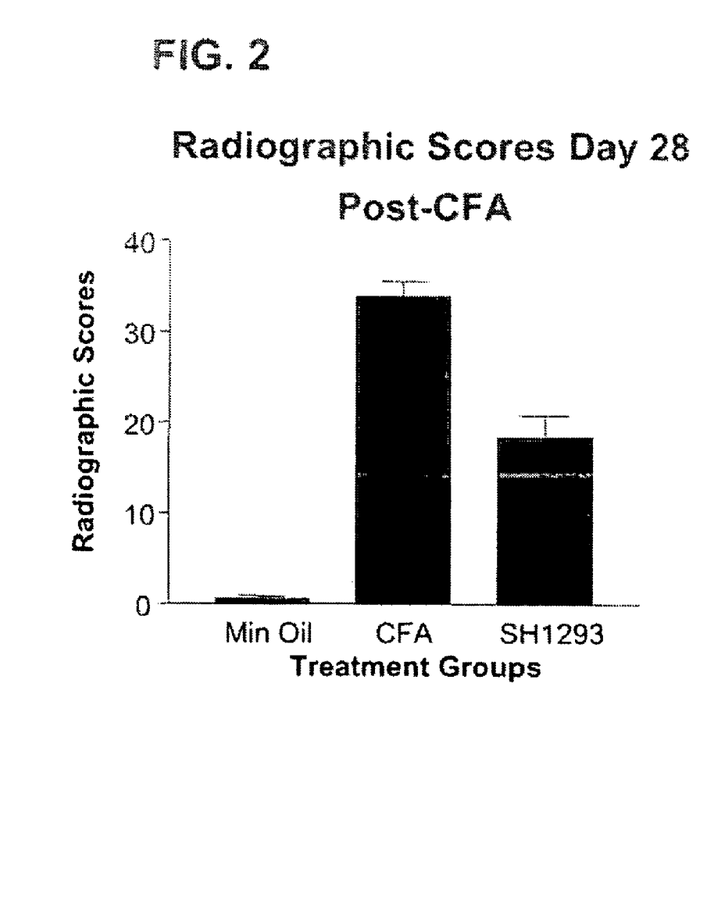
FIG. 2 is a graph depicting X-ray scores that were analyzed using a Kruskal Wallis Test with Bonferoni post-hoc test at day 28 post-CFA challenge.

While inflammation was decreased in these treatment groups, we observed a greater effect for these drugs in prevention of bone and cartilage destruction, as shown in FIG. 2A-C. X-ray scores were analyzed using a Kruskal Wallis Test with Bonferoni post-hoc test at day 28 post-CFA challenge; N=6; *, $P<0.05$; +, $P<0.001$. X-ray scores for hind limbs of AA rats treated with saline compared to SH1293 are significantly different ($P<0.05$). X-ray scores for both AA groups are significantly different from the non-arthritic mineral oil-treated rats on day 28 post-CFA challenge ($P<0.001$).

Figure 3:
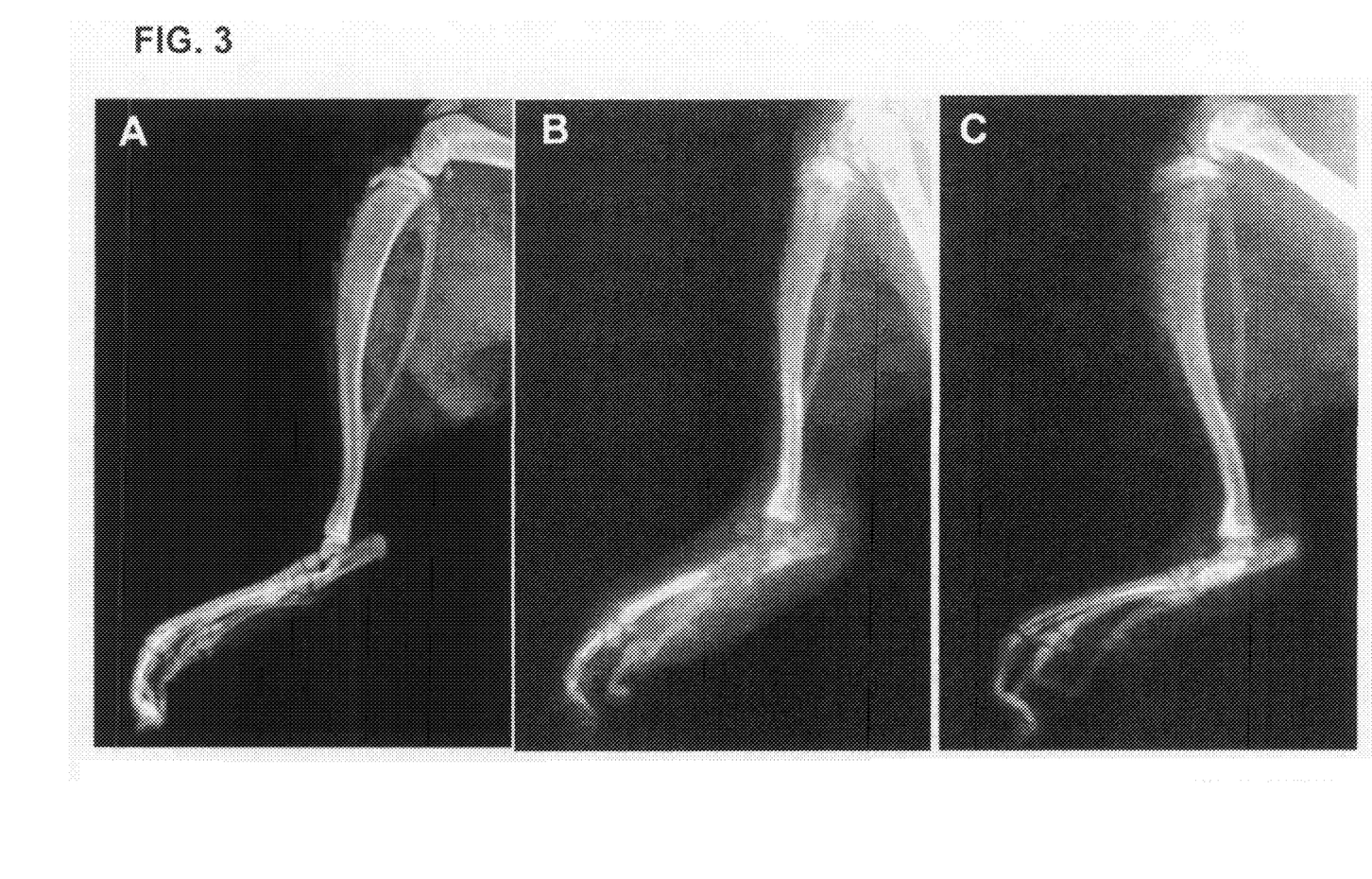
FIG. 3 shows radiographs of the hind limbs taken 28 days after challenge with CFA from arthritic rats treated with twice-daily injections of vehicle (FIG. 3B) and terbutaline and phentolamine treated rats (FIG. 3C) and untreated non-arthritic rats (FIG. 3A).

X-ray analysis revealed a significant decrease in bone destruction following combined terbutaline and phentolamine compared to AA rats treated with either of these drugs alone or compared to untreated AA rats, shown in FIG. 3. Radiographs of the hind limbs taken 28 days after challenge with CFA from arthritic rats treated with twice-daily injections of vehicle (FIG. 3B) and terbutaline and phentolamine (FIG. 3C) treated rats and untreated non-arthritic rats (FIG. 3A). Treatments were initiated at disease onset. Destructive joint changes were apparent in all arthritic animals. Treatment with terbutaline and phentolamine prevented much of the destructive joint changes observed in the saline treated AA rats.

These findings demonstrate anti-inflammatory and joint sparing properties of the combined treatment. Thus, combined adrenergic treatment would be effective in alleviating pain, as illustrated by manipulating the animals, taking dorsoplantar footpad width measurements, and observing that the AA animals treated with the combined adrenergic treatment continue to use their hind limbs.

Figure 4:
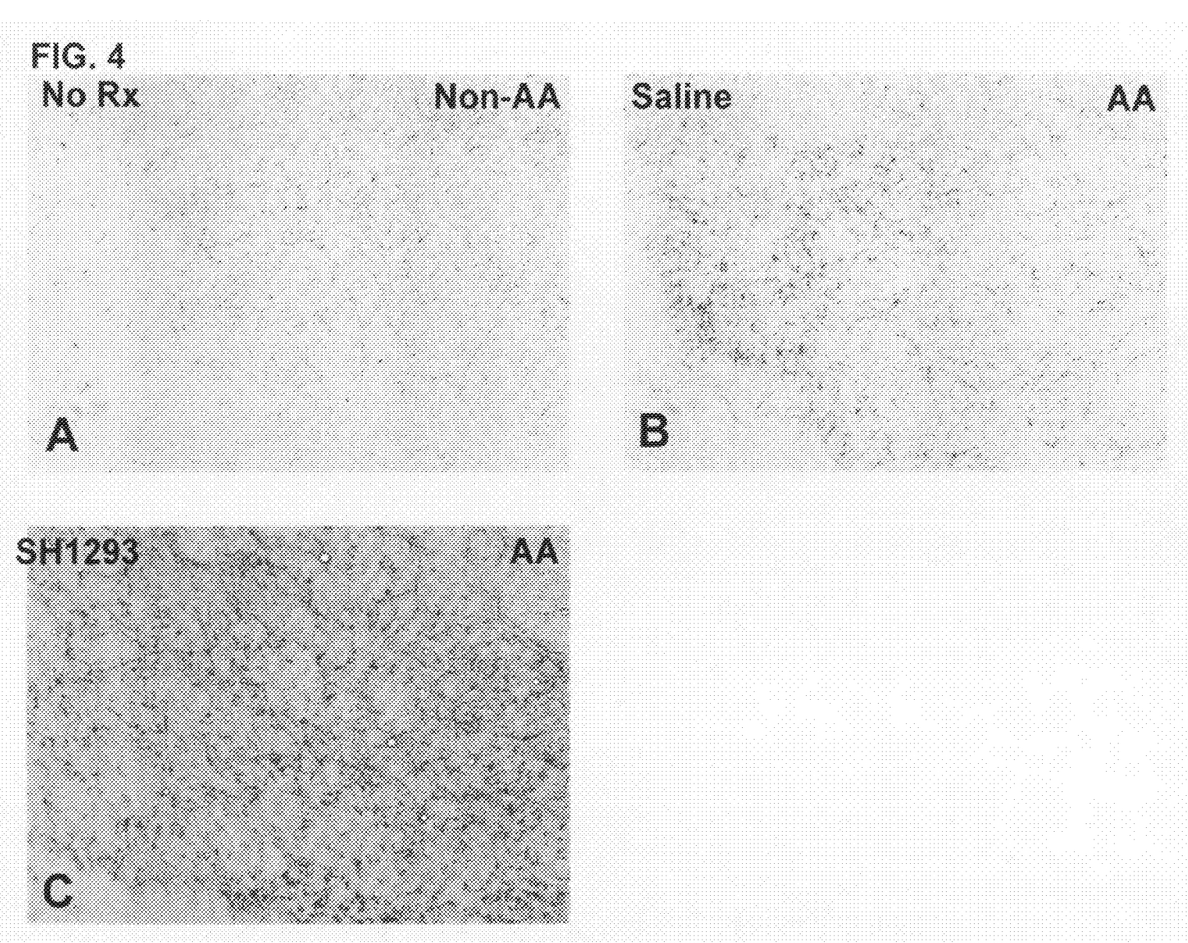
FIG. 4 shows photomicrographs of TH-immunoreactive axons in the dorsal horn of cervical spinal cord of untreated non-arthritic control rats (FIG. 4A), vehicle-treated AA rats (FIG. 4B), and terbutaline and phentolamine treated AA rats (FIG. 4C).

FIG. 4 shows photomicrographs of TH-immunoreactive axons in the dorsal horn of cervical spinal cord of untreated non-arthritic control rats (FIG. 4A), vehicle-treated AA rats (FIG. 4B), and terbutaline and phentolamine treated AA rats (FIG. 4C). TH-immunoreactive axons were increased throughout all laminae of the dorsal horn in arthritic vehicle- and combination adrenergic drug treated rats, albeit, with a greater increase with the adrenergic treatment. In the cervical spinal cord, more abundant TH-immunoreactive axons were observed in the dorsal spinal cord of AA rats compared to non-arthritic rats that received no treatment (FIGS. 4A-B). Treatment of arthritic rats with a combination of terbutaline and phentolamine resulted in a increase in TH-immunoreactive axons in the dorsal horn compared to vehicle-treated arthritic rats (FIGS. 4A-C).

Figure 5:
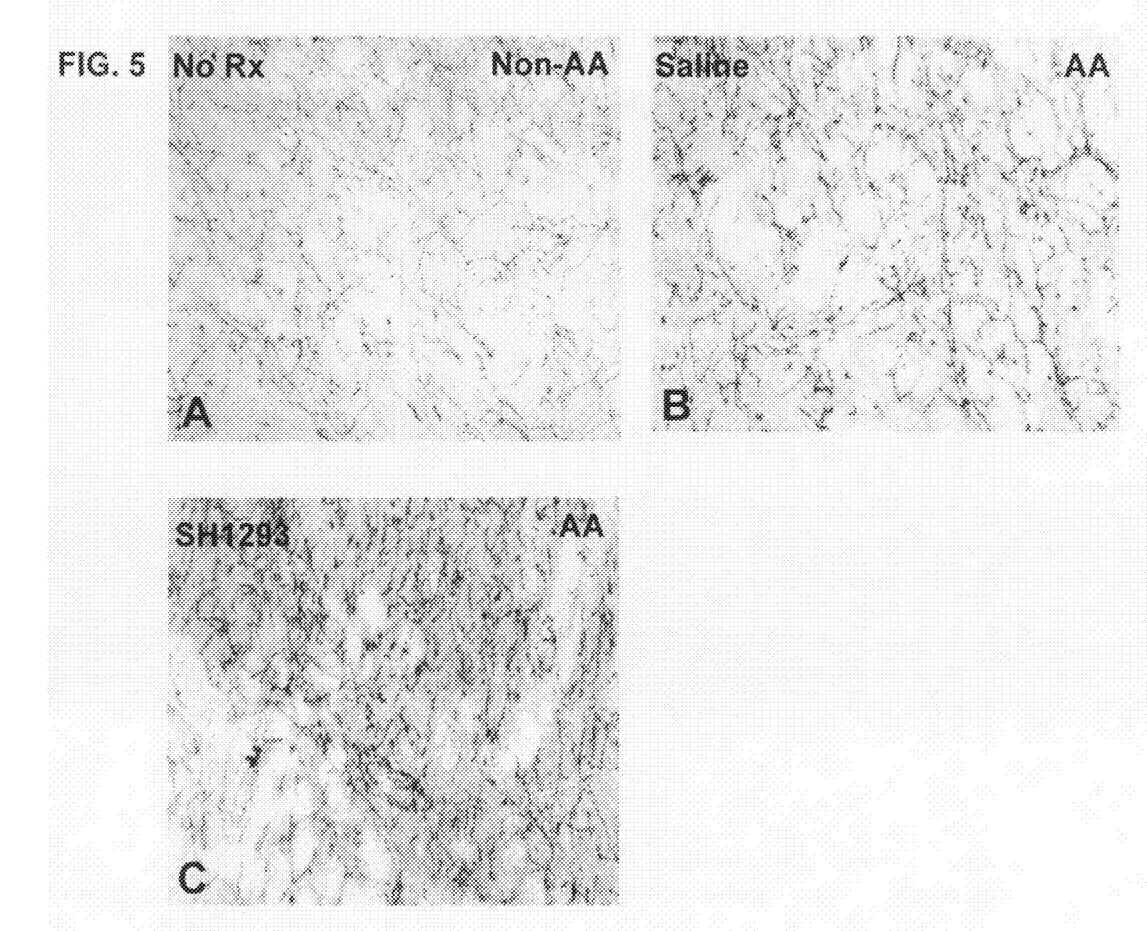
FIG. 5 shows photomicrographs of DBH-immunoreactive axons in the dorsal horn of cervical spinal cord of untreated non-arthritic control rats (FIG. 5A), vehicle-treated AA rats (FIG. 5B), and terbutaline and phentolamine treated AA rats (FIG. 5C).

FIG. 5 shows photomicrographs of DBH-immunoreactive axons in the dorsal horn of cervical spinal cord of untreated non-arthritic control rats (FIG. 5A), vehicle-treated AA rats (FIG. 5B), and terbutaline and phentolamine treated AA rats (FIG. 5C). TH-immunoreactive axons were increased throughout all laminae of the dorsal horn in arthritic vehicle- and combination adrenergic drug treated rats, albeit, with a greater increase with the adrenergic treatment. Similarly, DBH-immunoreactive axons in the dorsal horn of the cervical spinal cord were more abundant in vehicle-treated AA rats compared to non-arthritic untreated rats (FIGS. 5A-B). The combination adrenergic drug treatment in AA rats increased DBH-immunoreactive axons in the dorsal horn to a greater extent compared to vehicle-treated AA rats (FIGS. 5B-C). The increase in DBH-immunoreactive axons also occurred throughout all laminae in the dorsal horn.

Figure 6:
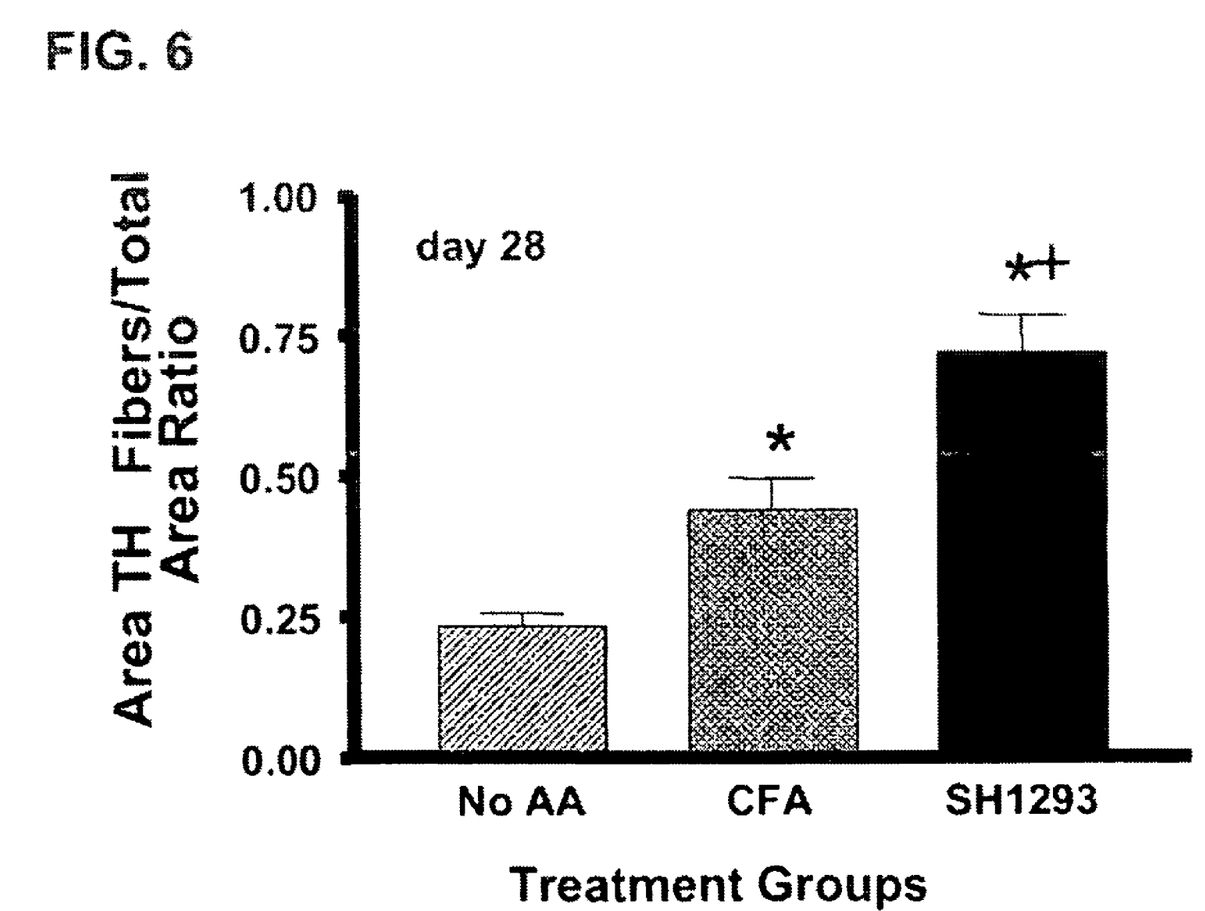
FIG. 6 shows quantification of TH-immunoreactive axons in the cervical dorsal horn or untreated non-arthritic control rats, vehicle-treated AA rats, and terbutaline and phentolamine treated AA rats.
Figure 7:
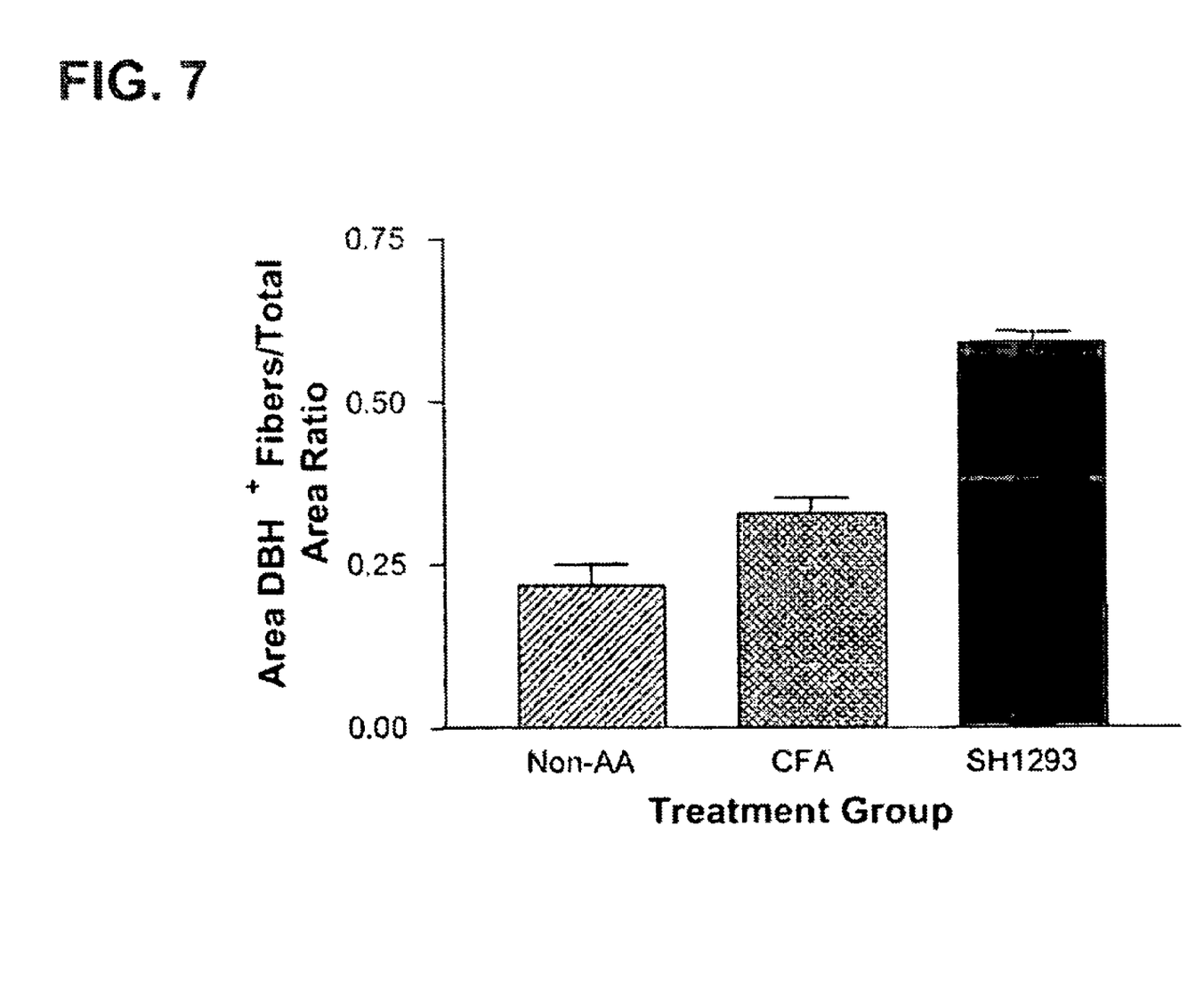
FIG. 7 shows quantification of DBH-immunoreactive axons in the cervical dorsal horn or untreated non-arthritic control rats, vehicle-treated AA rats, and terbutaline and phentolamine treated AA rats.

Quantitative image analysis demonstrated that the mean number of pixels per area occupied by TH-immunoreactive axons and DBH-immunoreactive axons in the dorsal horn of arthritic rats was significantly greater than that observed for non-arthritic rats (FIG. 6 and FIG. 7, P<0.05). FIG. 6 illustrates the quantification of TH-immunoreactive axons in the cervical dorsal horn or untreated non-arthritic control rats, vehicle-treated AA rats, and terbutaline and phentolamine treated AA rats. Quantitative image analysis demonstrated that the mean number of pixels per area occupied by TH-immunoreactive axons in the dorsal horn of arthritic rats was significantly greater than that observed for non-arthritic rats. (Mean±S.E.M., ANOVA with Bonferroni post-hoc test, P<p0.05 N=4).

FIG. 7 illustrates quantification of DBH-immunoreactive axons in the cervical dorsal horn or untreated non-arthritic control rats, vehicle-treated AA rats, and terbutaline and phentolamine treated AA rats. Quantitative image analysis demonstrated that the mean number of pixels per area occupied by DBH-immunoreactive axons in the dorsal horn of arthritic rats was significantly greater than that observed for non-arthritic rats. (Mean±S.E.M., ANOVA with Bonferroni post-hoc test, *P<0.05 N=6).

Administration of the combination adrenergic treatment to AA rats significantly increased the mean number of pixels per area occupied by TH-immunoreactive axons and DBH-immunoreactive axons compared to vehicle-treated AA rats (P<0.05) and to untreated non-arthritic rats (P<0.05). No differences were observed between TH- or DBH-immunoreactive activity between left and right sides of the dorsal horn spinal cords from any treatment group.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment, and best mode of the invention known to the applicant at this time of filing the application, have been presented and is intended for the purposes of illustration and description. It is not intended to be exhaustive nor limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out the invention.

We claim:

1. A method for treating pain in an animal comprising: administering to an animal a therapeutically effective dose of a composition comprising an $\alpha$-adrenergic antagonist; and a $\beta$-adrenergic agonist; wherein pain in the animal is decreased.

2. The method in claim 1, wherein the $\alpha$-adrenergic antagonist is an $\alpha_1$-adrenergic antagonist.

3. The method in claim 1, wherein the $\alpha$-adrenergic antagonist is an $\alpha_2$-adrenergic antagonist.

4. The method in claim 1, wherein the $\alpha$-adrenergic antagonist is selected from the group consisting of yohimbine, regitine, prazosin, doxazosin, tamsulosin, terazosin, octopamine, phenoxybenzamine, phentolamine, hydrochlorothiazide, 5-methyl urapidil, chloroethylclonidine, bunazosin, alfuzosin, urapidil, nicergoline, cyclazosin, fiduxosin, imiloxan, 2 idopropoxyidazoxan, 2-methoxyidazoxan, idazoxan, piperoxan, beditin, atipamezole, rawolscine, and ethoxyidazoxan.

5. The method in claim 1, wherein the $\beta$-adrenergic agonist is a $\beta_2$-adrenergic agonist.

6. The method in claim 1, wherein the $\beta$-adrenergic agonist is selected from the group consisting of terbutaline, metaproterenol, albuterol, isoetharine, pirbuterol, bitolterol, ritodrine, and salbutamol.

7. The method in claim 1, wherein the therapeutically effective dose of the composition comprises 1.0 to 10.0 mg of $\alpha$-adrenergic antagonist and 1.0 to 10.0 mg of $\beta$-adrenergic agonist.

8. The method in claim 1, wherein the therapeutically effective dose of the composition comprises 2.0 to 5.0 mg of $\alpha$-adrenergic antagonist and 2.0 to 5.0 mg of $\beta$-adrenergic agonist.

9. The method in claim 1, wherein the therapeutically effective dose of the composition comprises 1.25 to 2.5 mg of $\alpha$-adrenergic antagonist and 1.25 to 2.5 mg of $\beta$-adrenergic agonist.

10. The method in claim 1, wherein the animal is a mammal.

11. The method in claim 10, wherein the mammal is a human.

12. The method of claim 1, wherein the composition is administered in a form selected from the group consisting of pill, tablet, capsule, caplet, solution, suspension, syrup, suppository, aerosol and sustained-release.

13. The method of claim 1, wherein the route of administration is selected from the group consisting of sublingually, orally, intravenously, intramuscularly, rectally, parenterally, subcutaneously, and subdermally.

14. The method of claim 1, wherein the β-adrenergic agonist is administered in salt form.

15. The method of claim 14, wherein the β-adrenergic agonist salt form is selected from the group consisting of metaproterenol sulfate, terbutaline sulfate, albuterol sulfate, ioetharine hydrochloride, isoetharine mesylate, pributerol acetate, bitolterol mesylate, ritodrine hydrochloride, levalbuterol hydrochloride, and salmeterol.

16. The method of claim 1, wherein the α-adrenergic antagonist is administered in salt form.

17. The method of claim 16, wherein the α-adrenergic antagonist salt form is selected from the group consisting of phentolamine mesylate, regitine mesylate, prasozin, terazosin, doxazosin mesylate, and tamsulosin hydrochloride.

18. The method of claim 1, wherein the therapeutically effective dose is administered two times per day.

19. A method for treating rheumatoid arthritis comprising:
    administering to an animal an α-adrenergic antagonist; and
    administering to the animal a β-adrenergic agonist;
    wherein pain is decreased.

20. The method of claim 19, wherein the β-adrenergic agonist is administered followed by the α-adrenergic antagonist.

21. The method of claim 19, wherein the α-adrenergic antagonist is administered followed by the β-adrenergic agonist.

22. The method of claim 19, wherein the α-adrenergic antagonist and β-adrenergic agonist are administered in the same 24-hour time period.

23. The method of claim 19, wherein the α-adrenergic antagonist and β-adrenergic agonist are administered in the same one-hour time period.

24. A composition for treating pain in humans comprising:
    an α-adrenergic antagonist; and
    a β-adrenergic agonist.

25. A composition useful in the treatment of pain comprising:
    0.01 mg to 100.0 mg of phentolamine; and
    0.01 mg to 100.0 mg of terbutaline.

* * * * *